(12) United States Patent
Kirchhofer

(10) Patent No.: US 7,374,558 B2
(45) Date of Patent: May 20, 2008

(54) INJECTION DEVICE COMPRISING A STERILELY ATTACHED INJECTION NEEDLE AND A NEEDLE SUPPORT AND AMPOULE FOR SUCH AN INJECTION DEVICE

(75) Inventor: Fritz Kirchhofer, Sumiswald (CH)

(73) Assignee: TechPharma Licensing AG, Burgdorf (CH)

( * ) Notice: Subject to any disclaimer, the term of this patent is extended or adjusted under 35 U.S.C. 154(b) by 442 days.

(21) Appl. No.: 10/354,882

(22) Filed: Jan. 30, 2003

(65) Prior Publication Data
US 2003/0144633 A1 Jul. 31, 2003

(30) Foreign Application Priority Data
Jan. 30, 2002 (DE) .................. 102 03 598

(51) Int. Cl.
*A61M 5/24* (2006.01)
*A61M 5/32* (2006.01)

(52) U.S. Cl. ....................... 604/200; 604/194
(58) Field of Classification Search ................ 604/187, 604/192–203, 110, 263
See application file for complete search history.

(56) References Cited

U.S. PATENT DOCUMENTS

| 3,524,445 | A | * | 8/1970 | Frieze ................. 604/200 |
| 3,895,633 | A | * | 7/1975 | Bartner et al. ......... 604/192 |
| 4,861,335 | A | * | 8/1989 | Reynolds .............. 604/88 |
| 4,936,841 | A | * | 6/1990 | Aoki et al. ............ 604/413 |
| 5,281,198 | A | * | 1/1994 | Haber et al. .......... 604/86 |
| 5,312,366 | A | * | 5/1994 | Vailancourt .......... 604/192 |
| 5,342,346 | A | * | 8/1994 | Honda et al. .......... 604/413 |
| 5,478,337 | A | * | 12/1995 | Okamoto et al. ....... 604/413 |
| 5,873,462 | A | * | 2/1999 | Nguyen et al. ........ 206/366 |
| 5,971,966 | A | * | 10/1999 | Lav ..................... 604/263 |
| 6,022,339 | A | * | 2/2000 | Fowles et al. ......... 604/411 |
| 6,537,263 | B1 | * | 3/2003 | Aneas .................. 604/412 |
| 6,736,800 | B2 | * | 5/2004 | Rindlisbacher ........ 604/192 |
| 6,893,420 | B2 | * | 5/2005 | Arnisolle ............. 604/135 |

FOREIGN PATENT DOCUMENTS

EP 0 695 554 A2 2/1996

* cited by examiner

*Primary Examiner*—Kevin C. Sirmons
*Assistant Examiner*—Andrew Gilbert
(74) *Attorney, Agent, or Firm*—David E. Bruhn

(57) ABSTRACT

An injection device including a sterile injection needle, the injection device including a container for an injectable product including an outlet for the product at a front end sealed by a membrane, the injection needle, which has a front needle portion facing away from the container for injecting into tissue and a rear needle portion which, in an initial state of the injection device lies opposite and faces the membrane and which is injected through the membrane into the container for an injection, a needle support which holds the injection needle in a central needle portion, and a casing which supports the needle support and the container and movably guides them relative to each other for piercing the membrane, wherein, in the initial state of the injection device, the needle support forms a sterile chamber for the rear needle portion, the chamber sealed by a sealing element on a rear side of the chamber facing the outlet of the container, and wherein the front end of the container for piercing the membrane penetrates through the sealing element into the sterile chamber.

10 Claims, 3 Drawing Sheets

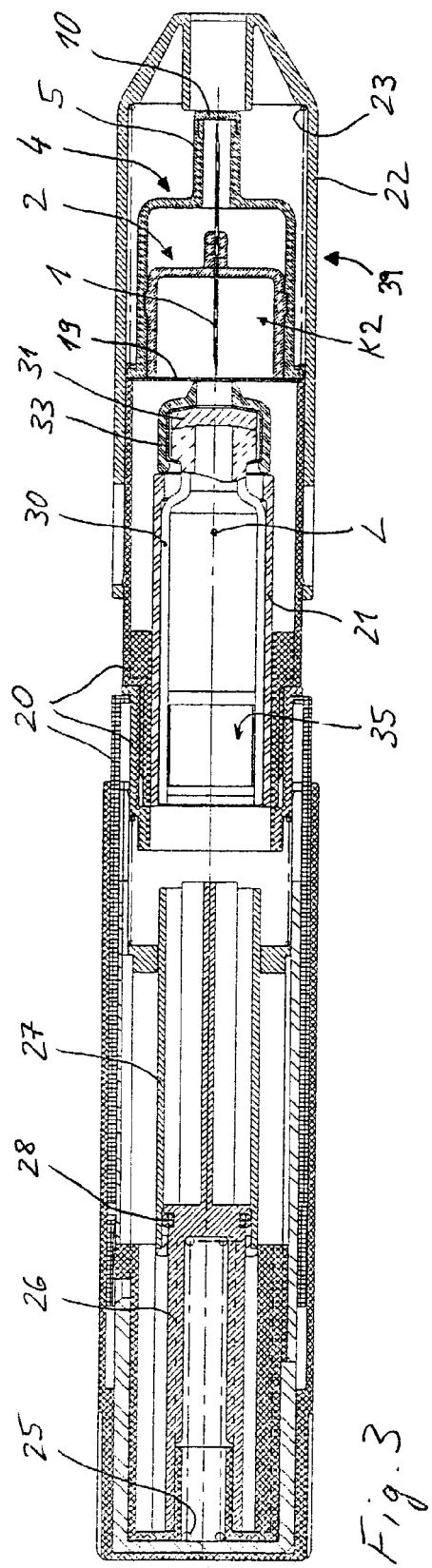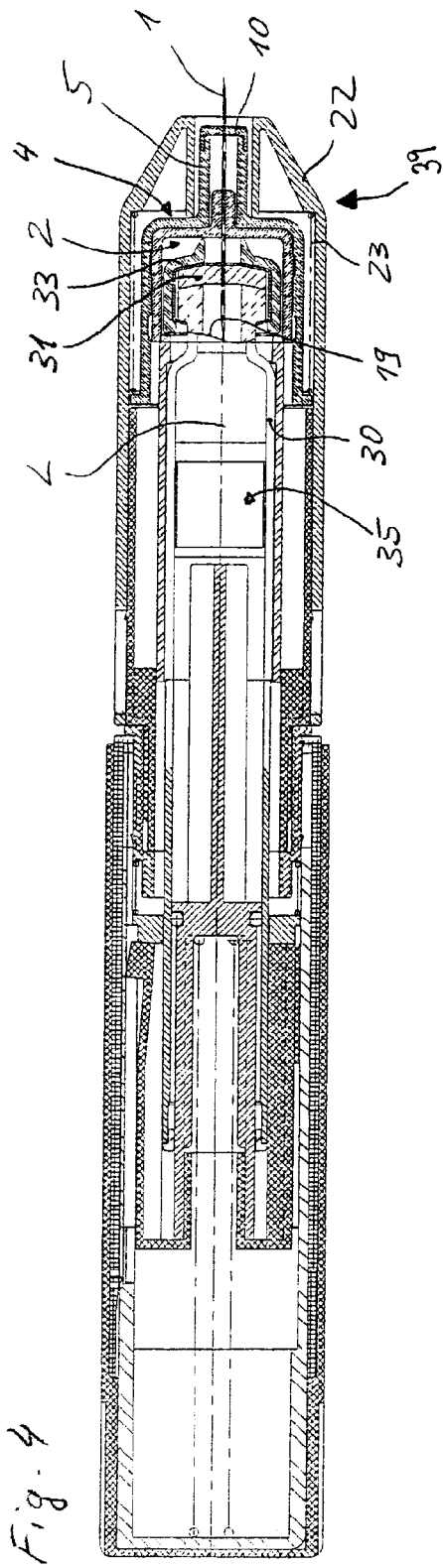

INJECTION DEVICE COMPRISING A STERILELY ATTACHED INJECTION NEEDLE AND A NEEDLE SUPPORT AND AMPOULE FOR SUCH AN INJECTION DEVICE

PRIORITY CLAIM

This utility patent application claims the priority of the German patent application, serial number DE 102 03 598.9, filed on Jan. 30, 2002; subject matter of which is incorporated herewith by reference.

BACKGROUND

The invention relates to an injection device comprising an injection needle which is connected to the injection device and which, when connected, is situated in or on the injection device in a sterile environment. The invention further relates to a needle support suitable for sterilely attaching an injection needle into or onto an injection device. The subject of the invention is also an ampoule for an injection device, designed for establishing a fluid connection to a sterilely attached injection needle.

On way of making the handling of injection devices easier and safer is to pre-attach the injection needle onto or into the injection device during manufacture. The user does not have to worry about attaching the needle himself. This simplifies handling and reduces the risk of injury. The danger of damaging the needle due to careless handling by the user and the danger of the needle being incorrectly attached are also eliminated. The sterility of the pre-attached injection needle must, however, be ensured.

An auto-injection device is known from EP 0 695 554 A2, into whose casing the injection needle is inserted by means of a needle support. The needle support holds the injection needle in a central needle portion and orients it in the longitudinal direction towards an ampoule filled with an injectable product. The needle projects from the needle support on both sides, from a front needle portion and a rear needle portion. The injection needle is injected into and under the human skin via its front needle portion. The fluid connection between the ampoule and the injection needle is not established until the exact time of injection, by advancing the ampoule firstly against the needle support and then, together with the needle support, relative to the casing of the injection device. When the ampoule is advanced relative to the needle support, the rear needle portion of the injection needle penetrates a membrane which seals a product outlet of the ampoule. In order to ensure the sterility of the injection needle up until a first injection, the entire injection device must be sterilized in its interior. Sterilization is therefore complicated and expensive.

SUMMARY

It is an object of the invention to ensure the sterility of an attached injection needle in an injection device in a simple and cost-effective way. More particularly, the intention is to provide an injection device comprising a sterilely attached injection needle. Furthermore, the intention is to provide a needle support which makes it easier to keep the injection needle sterile. It is also an object of the invention to design an ampoule in such a way that it is suitable for use in an injection device in accordance with the invention and, in one embodiment, for co-operating with a needle support in accordance with the invention.

An injection device comprising a sterilely attached injection needle, such as the invention relates to, comprises a casing, a container for an injectable product, the injection needle and a needle support. The container comprises an outlet at a front end, for the product, the outlet being sealed tightly by a membrane. Insulin and growth hormones may be cited as examples, but not exclusive examples, of products. The needle support, like the container, is also supported by the casing and ensures that the injection needle is correctly oriented. The injection needle comprises a front needle portion for injecting into tissue and a rear needle portion which points towards the outlet and the membrane of the container and is injected through or penetrates the membrane for an injection, in order to establish a fluid connection between the container and the injection needle. The injection device assumes an initial state when the injection needle is attached onto or into the casing of the injection device in a position oriented towards the container and the casing, but a fluid connection to the container has not yet been established. In this state, the needle support forms a sterile chamber for the rear needle portion. A sealing element seals this chamber on a rear side of the chamber facing the outlet of the container. The membrane of the container is pierced by the container penetrating through the sealing element into the chamber, preferably only in the course of an injection, and the fluid connection between the container and the injection needle is thus established. Because a sterile chamber is formed for the rear needle portion in accordance with the invention, it is no longer necessary for the sterility of the injection needle to sterilize the entire injection device. Only the chamber for the injection needle formed by the needle support has to be sterile.

The relative movement which the needle support and the container perform towards each other for the purpose of establishing the fluid connection is guided by the casing. The relative movement preferably takes place in the longitudinal direction of the injection needle. In preferred embodiments, the needle support is immovably connected to the casing, such that it cannot be moved relative to the casing towards the container and preferably also not in the opposite direction, while the casing forms a linear guide for the container. Supporting and guiding the needle support and the container in this way is generally realized inherently in auto-injection devices representing examplary embodiments of the invention, such that no modifications or no appreciable modifications have to be made to such injection devices in order to ensure the sterility of the rear needle portion of the injection needle in a way in accordance with the invention.

The invention is not, however, restricted to the embodiment described above. For instance, it is also possible to connect the container immovably to the casing with respect to the longitudinal direction of the injection needle, while the casing movably guides the needle support, such that the injection needle pierces the membrane of the container through a movement of the needle support relative to the casing and the container. In such an embodiment, the needle support can, for example, be connected to a needle covering device. The connection between the needle support and the needle covering device can be designed such that the needle covering device slaves the needle support when it is retracted relative to the casing, until the injection needle has pierced the membrane of the container. The needle support, together with the needle covering device, can move backwards against a stopper formed by the casing or by the container. Once the needle support reaches the stopper position, the connection between the needle support and the needle covering device is released and when the needle covering device is retracted further relative to the casing, the injection needle is exposed through a front opening of the needle covering device. When injecting, the needle covering device can perform the entire backward movement continuously in one movement.

The invention is particularly advantageous in disposable injection devices which are disposed of once the container has been emptied, or are returned to the manufacturer in a cycle of processing and re-use. In the case of such devices, only the manufacturer attaches the injection needle, for example by inserting the needle support into the casing of the device. Precisely with such devices, the storage periods in the initial state, i.e., with an attached injection needle, last a long time, such that ensuring the sterility of the injection needle in accordance with the invention is particularly advantageous.

The invention may preferably be used in injection devices for products to be administered by the user, but is not restricted to such applications. Equally, the invention is not restricted to being used in the disposable devices cited above. It can also advantageously be used in injection devices in which during use the injection needle is replaced one or more times, in order to always have a new, sterile injection needle after each replacement, for example in combination with replacing an empty product container.

Needle supports in accordance with the invention, which in the market can also be delivered to users as separate parts, detached from an injection device, are described herein. The needle support described in connection with the injection device can be formed a holding body which holds the injection needle in a central needle portion and from which a front needle portion and a rear needle portion project, and a hollow-cylindrical outer body which accommodates the holding body so as to be movable in an advancing direction in the longitudinal direction of the injection needle and which forms a sterile front chamber for the front needle portion, the chamber being pierced by the injection needle by means of a movement which the holding body performs in the advancing direction, relative to the outer body, wherein at least one of the bodies forms a sterile rear chamber for the rear needle portion, the chamber being sealed by a sealing element on its rear side facing away from the front needle portion, and wherein the front chamber is sealed by a septum which is pierced by the injection needle when the holding body is moved in the advancing direction, relative to the outer body The sealing element which sterilely seals a rear side of the chamber for the rear needle portion can be a film, in one preferable example a so-called peel film, which is fixed to the needle support, in particular fixed in a material lock, once the needle support has been produced. The sealing element can also in principle be made of the same material as the part of the needle support forming the sterile chamber, and can be manufactured together with this part as one piece, as long as it is ensured that the container penetrates through such a sealing element into the chamber and the membrane of the container is simultaneously pierced by means of the injection needle. In some preferable embodiments it is designed as a separately fixed film, since the two functions of the sealing element, namely to sterilely seal the chamber and to be easily punctured or pierced by the penetrating container, may be realized more easily with such a film than if it is designed as one piece. A compromise between a subsequently fixed film and a sealing element, which can also be designed as a film, produced as one piece together with at least a part of the needle support, would be to form the sealing element from a material of its own and to integrally shape it together with the needle support or the part of the needle support forming the chamber for the rear needle portion.

The needle support may preferably also forms a sterile chamber for the front needle portion of the injection needle, in particular if the needle support is a part which can be handled and in particular sold separate from a particular injection device. In principle, however, it would alternatively be conceivable for the needle support to form only the chamber for the rear needle portion and for the front needle portion to be sterilized separately.

If the needle support advantageously also forms the sterile chamber for the front needle portion, then this sterile front chamber can be formed by a protective cap which is detachably connected to a holding body of the needle support which holds the injection needle, such that it can be removed from the holding body for the purpose of injecting. The connection between the holding body and the protective cap must exhibit sufficient impermeability to ensure the sterility of the front needle portion.

In another preferred embodiment, an enveloping body of the needle support forms a single sterile chamber in which the entire injection needle is arranged. Such an enveloping body is sealed on its rear side by the sealing element already cited. On its front side, in an extension of the front needle portion, it comprises another sealing element which is pierced by the front needle portion during injection. This front sealing element is preferably a septum which still sterilely seals the chamber after it has been repeatedly pierced. Such septa are known in their own right, for example as sealing membranes for ampoules. One particularly preferred way of manufacturing it, namely manufacturing it integrally together with the enveloping body of the needle support in a bi-component injection molding process, is described for other components in DE 100 06 560.0, to which reference is made as an advantageous example of manufacturing the enveloping body and the front sealing element. In principle, the rear sealing element of the needle support can also be obtained in the same way.

If the needle support comprises the enveloping body cited above, then a further, inner body which holds the injection needle is movably arranged in such an enveloping body in such a way that the front sealing element is punctured by the injection needle when the inner body is moved relative to the enveloping body.

An ampoule which can form the container of the injection device in accordance with the invention and which is suitable for co-operating with needle supports in accordance with the invention also forms a subject of the present invention.

At one end of the ampoule, which forms the product outlet of the ampoule, the ampoule comprises a separating means by which a tensioned film can be cut through by means of a movement of the ampoule directed perpendicular to the film. The ampoule in accordance with the invention is therefore designed for co-operating with a needle support which, when detached, comprises a film as a sealing element on its rear side facing the ampoule. That it is a tensioned film means that the film does not give under the pressure of the separating means so far that it can no longer be cut through by the separating means. The separating means forms a separating edge, at a radial distance, about a longitudinal axis of the product outlet which preferably corresponds to the longitudinal axis of the injection needle, said separating edge tapering off sharply and pointedly towards the film, such that it fulfils its function of puncturing, preferably piercing or cutting through, the film when it strikes the film, and the film is cut through along the separating edge. The separating edge may preferably run in an extension of the outlet of the ampoule and, in one preferred embodiment, designed circumferentially, advantageously forming an inner cross-section which corresponds to the cross-section of the product outlet.

BRIEF DESCRIPTION OF THE DRAWINGS

Examplary embodiments of the invention will now be illustrated by reference to the accompanying Figures. Features disclosed by the examplary embodiments, each individually and in any combination of features, advantageously develop the subjects of the invention. Moreover, advantageous combinations of one or more features of one examplary embodiment with one or more features of another examplary embodiment are also disclosed.

FIG. 3 depicts an injection device comprising the attached needle support and the ampoule in the position in FIG. 1;

FIG. 4 depicts the injection device comprising the needle support and the ampoule in the position in FIG. 2;

DETAILED DESCRIPTION

Figures 1, 2:
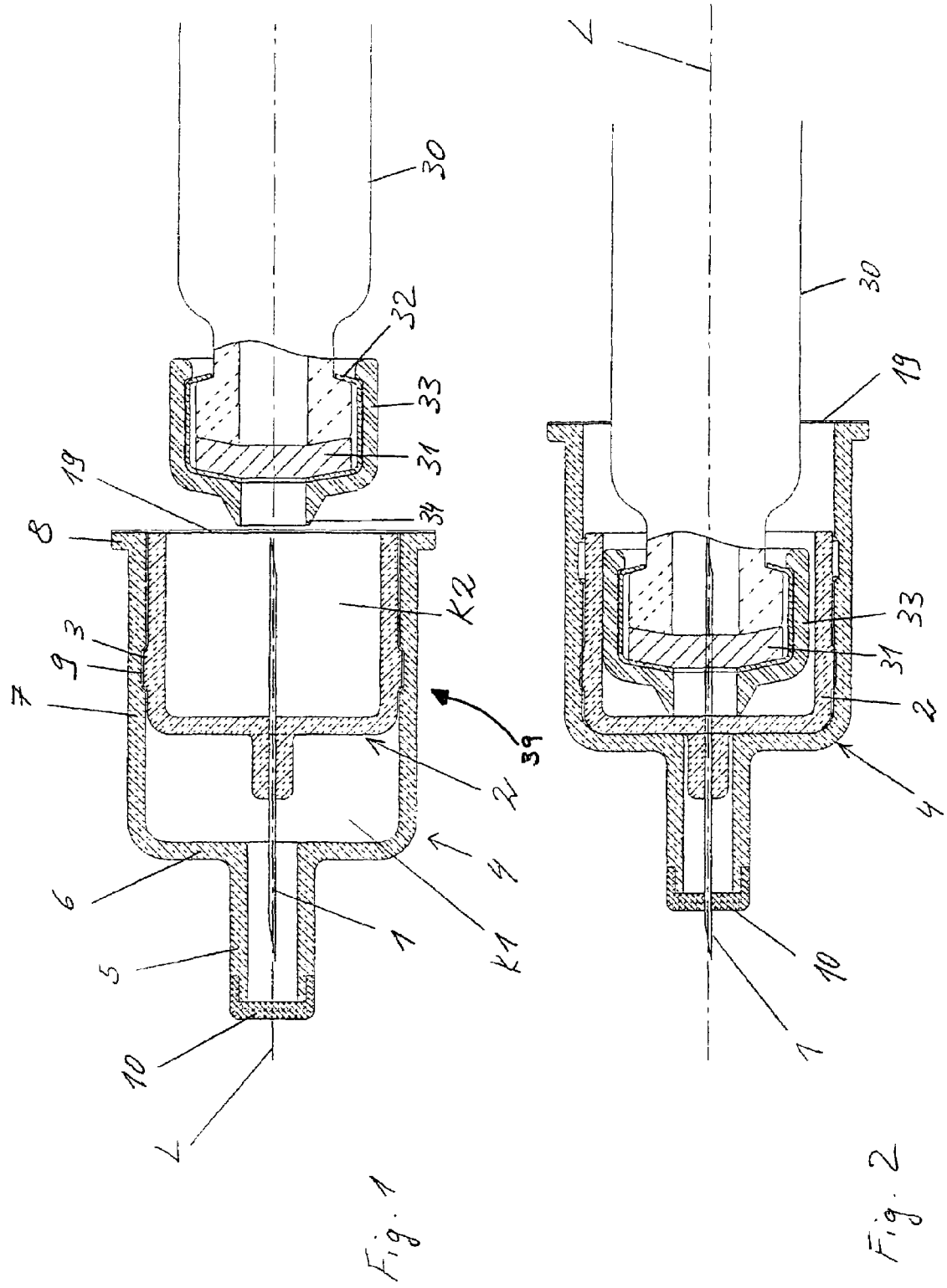
FIG. 1 depicts a needle support in a first examplary embodiment, and an ampoule in a position orientated for establishing a connection.
FIG. 2 depicts the needle support and the ampoule of FIG. 1, when connected.

FIG. 1 shows a needle support and a container formed by an ampoule 30, in a longitudinal section. The needle support is in two parts and is formed by an inner body 2 and an outer body 4. The outer body 4 is substantially hollow-cylindrical and accommodates the inner body 2. The inner body 2 holds an injection needle 1 formed by a hollow steel cannula having two pointed ends. The injection needle can for example be a 30 G or 31 G needle. Because of its holding function, the inner body 2 will be referred to in the following as the holding body. It holds the injection needle in a central needle portion. A front needle portion and a rear needle portion each project freely from the central needle portion, the holding region of the holding body 2. The injection needle 1 extends completely straight along a longitudinal axis L. In FIG. 1, the needle support 39 and the ampoule 30 are each shown in a position which they assume when attached into an injection device. This state corresponds to an initial state before the injection needle 1 is used a first time. In the initial state, the needle support 39 forms a sterile protective sleeve for the injection needle 1. The injection device can be stored in the initial state, in particular over a long period of time, in view of the sterility of the injection needle 1, but on the other hand is ready for an injection without further handling to attach it.

The initial state, which in FIG. 1 is only shown by way of the parts essential to the invention, separate from a particular injection device, is illustrated in FIG. 3 by way of a complete installation using the example of an auto-injection pen. A casing 20 of the pen supports the needle support 39 and the ampoule 30 in the initial position shown in FIG. 1.

The holding body 2 has the shape of a circular-cylindrical pot. A circular-cylindrical surface of the holding body 2 surrounds the rear needle portion of the injection needle 1 and protrudes slightly beyond the rear tip of the needle. The injection needle 1 protrudes centrally through the pot base of the holding body 2 and is immovably held there along its longitudinal axis L.

The outer body 4 forms an enveloping body for the holding body 2 and the injection needle 1. This enveloping body 4 is hollow-cylindrical with a front hollow-cylindrical part 5 and a rear hollow-cylindrical part 7 which exhibits a larger cross-section than the front hollow-cylindrical part 5. The holding body 2 is slidably accommodated in the rear hollow-cylindrical part 7 along the longitudinal axis L. The front needle portion of the injection needle 1 protrudes from the base of the holding body 2 into the front hollow-cylindrical part 5 of the enveloping body 4. The two hollow-cylindrical parts 5 and 7 of the enveloping body 4 are concentric with respect to the injection needle 1. A radial transition collar 6 connects the front hollow-cylindrical part 5 to the circular-cylindrical rear hollow-cylindrical part 7. Due to the significant difference in the cross-sections of the two hollow-cylindrical parts 5 and 7, the enveloping body 4 of the examplary embodiment also exhibits the shape of a pot formed substantially by the rear hollow-cylindrical part 7. The front hollow-cylindrical part 5 acts as a slim continuation of the rear hollow-cylindrical part 7. The enveloping body 4 comprises an outer flange 8 on its rear side facing the ampoule 30. The flange 8 serves to attach the needle support 39 into the injection device.

In alignment with the injection needle 1, the enveloping body 4 comprises a sealing element 10 at its front end, which element can be pierced by the injection needle 1. The sealing element 10 is formed by a septum and covers the entire cross-section of the otherwise simply straight front hollow-cylindrical part 5. The rear side of the enveloping body 4 sealed by a sealing element 19. The sealing element 19 is a thin film, said film spanning the hollow-cylindrical cross-section of the enveloping body 4, which is open towards the rear, and being connected to the rear facing area of the enveloping body 4, completely and tightly surrounding it, for example by means of an adhesive connection. The enveloping body 4, the two sealing elements 10 and 19 opposing each other along the longitudinal axis L, and the connection between the sealing elements 10 and 19 and the enveloping body 4 are such that a sterile chamber is formed by the enveloping body 4 and the two sealing elements 10 and 19. This essentially unitary chamber is sub-divided into a front partial chamber K1 and a rear partial chamber K2 by the base of the holding body 2. The partial chambers K1 and K2 are subject, however, to mutual gaseous exchange. The holding body 2 does not fulfil a sealing function. However, the bisection into the enveloping body 4 and the holding body 2, and the fact that the holding body 2 can move relative to the enveloping body 4, means that the injection device is ready for an injection and that no further handling with regard to the injection needle 1 is necessary, once the needle support 39 has been attached, i.e. inserted.

The ampoule 30 is substantially linearly cylindrical with an open rear end (not shown) into which a piston is inserted in a known way, said piston sealing the ampoule to the rear such that an injectable product contained in the ampoule cannot escape. At a front end of the ampoule 30, lying directly adjacent and opposite to the needle support 39 along the longitudinal axis L in the initial state shown in FIGS. 1 and 3, the ampoule 30 comprises an outlet through which the ampoule 30 can be emptied by advancing the piston. The outlet is tightly sealed by a membrane 31. A clamp 32 serves to fix the membrane 31 to the end of the ampoule 30. To this extent, the ampoule 30 can correspond to known ampoules.

However, at the front end of the ampoule, the ampoule 30 comprises a separating means 33 which forms a foremost end of the ampoule 30 in the longitudinal direction L. This foremost end is a separating edge 34 surrounding the longitudinal axis L at a radial distance. The separating means 33 as a whole is hollow-cylindrical. It is clamped onto the front end of the ampoule by gripping behind the clamp 32 via a rear collar protruding radially inwards and in this way longitudinally tensioning the separating means 33 against the membrane 31. From its hollow-cylindrical part surrounding the neck of the ampoule 30, the separating means 33 firstly protrudes at its front end substantially radially inwards up to about the height of the extended, intended outlet of the ampoule 30. A circumferential continuation protrudes in the longitudinal direction L from this inwardly protruding circumferential collar, said continuation tapering in the longitudinal direction L towards a front tip, in such a way that the separating edge surrounding the longitudinal axis L is formed. Up to its separating edge 34, the separating means 33 forms a linearly cylindrical extension of the outlet cross-section of the ampoule 30.

In the initial state, the holding body assumes a rearmost position with respect to the enveloping body 4, in which position the rear needle tip of the injection needle 1 comes to rest directly in front of the rear sealing element 19. In order to prevent an undesired movement of the holding body 2 relative to the enveloping body 4 and out of the rearmost position, the initial position, a positive mesh, or connection, exists between the holding body 2 and the enveloping body 4. The positive connection is formed by a recess 9 and a protrusion 3 meshing, connecting to or joining with the recess, which are formed on opposing surface areas of the holding body 2 and the enveloping body 4 facing each other. The positive mesh can be released by a force directed in the longitudinal direction L, which however has to be significantly larger than the forces which can usually occur during storage, transport and handling of the injection device, up until injection.

The auto-injection device of the examplary embodiment is a disposable injector provided by the manufacturer in an initial state as shown in FIG. 3. A casing of the injection device is formed from a number of parts which are non-shiftably and non-rotatably connected to each other with respect to a common longitudinal axis which corresponds to the longitudinal axis L of the injection needle 1, and are therefore referred to in their entirety as the casing 20. The ampoule is inserted into a sleeve-shaped ampoule holder 21. The ampoule holder 21 is supported by the casing 20 and linearly guided in the longitudinal direction L. The ampoule 30 is inserted into the ampoule holder 21 from the rear, in the longitudinal direction L, up until a front stopper.

A needle cover 22, which may be shifted back and forth along the longitudinal axis L, is fixed to the casing 20 at the front end of the casing 20. The needle cover 22 is a sleeve with a base at its front end in which an opening is centrally relieved for the injection needle 1 and the front hollow-cylindrical part 5 of the needle support 39. The needle support 39 is fixed to the casing 20 by means of the needle cover 22. It is fixed or attached such that the enveloping body 4 is pressed via its rear facing area against a front facing area of the casing 20, such that the outer rim of the rear sealing element 19 comes to rest between facing areas pressed against each other. By attaching it in this way, the outer flange 8 of the enveloping body 4 forms a fixing element, by tensioning a pressure spring 23 between the outer flange 8 and the opposing base of the needle cover 22 in the longitudinal direction. The pressure spring 23 presses the needle cover 22 relative to the casing 20 into its front position shown in FIG. 1, in which it directly covers the injection needle 1 and the needle support 39.

Viewed from the needle support 39, behind the ampoule 30, a drive means for the piston 35 arranged in the ampoule 30 is accommodated in the casing. The drive means comprises a drive element 25 formed by a pressure spring, a piston rod 26 and an ampoule drive rod 27. The drive spring 25 is tensioned between the piston rod 26 and a rear base of the casing 20 and can be triggered by means of an operating element. The piston rod 26 and the ampoule drive rod 27 are supported in the casing 20 such that they can be linearly moved relative to the casing 20, jointly and each individually, towards the ampoule 30 and the piston 35. The ampoule drive rod 27 surrounds a front part of the piston rod 26 concentrically. The piston rod 26 and the ampoule drive rod 27 are positively meshed with each other, wherein said mesh can be released by a force directed along the longitudinal axis L towards the piston 35. A mesh element providing the positive mesh is indicated by 28. With respect to the drive means, reference is made to DE 198 22 031 C2 in which the drive means, to be understood merely as an example with respect to the invention, is described in detail.

The functionality of the injection device will now be illustrated by way of FIGS. 3 and 4, and reverting to FIGS. 1 and 2:

For injecting, the user grips the injection device in the region of the casing 20 and presses the needle cover 22, against the pressure of the pressure spring 23, as far as the collar 6 of the enveloping body 4. With the needle covering device 22 in this position, the injection device is pressed against the skin at the injection point and the drive means is triggered. This releases a latch on the piston rod 26. The drive spring 25 advances the piston rod 26 towards the piston 35. Due to the mesh provided by the mesh element 28, the ampoule drive rod 27 is slaved by the piston rod 26. In said joint shifting movement, the ampoule drive rod 27 firstly pushes against the rear facing area of the ampoule 30 and advances the ampoule 30, and therefore jointly the ampoule holder 21, relative to the casing 20 and in particular relative to the needle support 39, along the longitudinal axis L. In the initial state of the injection device, the separating edge 34 of the separating means 33 exhibits only a very small distance from the rear sealing element 19. Due to the forward movement of the ampoule 30, the separating edge 34 therefore punctures the rear sealing element 19 directly after the movement of the ampoule is introduced. The sealing element 19 is cut through in such a way that when the ampoule 30 is advanced further, the edge of the injection needle 1 passes over the resultant exposed flap-like portion of the sealing element 19 at the separation point, such that the rear tip of the injection needle comes to rest free from the membrane 31.

The ampoule 30, more precisely the separating means 33, penetrates further into the opened rear chamber K2 under the pressure of the ampoule drive rod 27, until the separating edge 34 pushes against the base of the holding body 2. At the latest when this stopper position against the holding body 2 has been reached, the injection needle 1 has also penetrated the membrane 31 and protrudes into the ampoule 30, such that the fluid connection between the ampoule 30 and the injection needle 1 is established.

Under the continuing pressure of the ampoule drive rod 27, the ampoule 30 advances the holding body 2 via the separating means 33 and relative to the enveloping body 4. During this joint advancing, the injection needle 1 penetrates the front sealing element 10. The joint movement of the ampoule 30 and the holding body 2 is complete as soon as the base of the holding body 2 pushes against the collar area 6 of the enveloping body 4. In this stopper position, the injection needle protrudes as far beyond the front sealing element 10 as is necessary for subcutaneously administering the product. The shifting movement of the ampoule 30 relative to the casing 20 is complete once the stopper position has been reached.

The drive element 25 presses further against the piston rod 26. Since, however, it is not possible to advance the ampoule drive rod 27 any further, the positive connection provided by the mesh element 28 is released. The piston rod 26 is then advanced further relative to the ampoule drive rod 27. In this second phase of its movement, the piston rod 26 advances the piston 35 in the ampoule 30 towards the product outlet, such that product is delivered through the injection needle 1. FIG. 4 shows the injection device while the product is being delivered, before the piston 35 has reached its foremost position in the ampoule 30.

Once the ampoule 30 has been emptied, the injection needle 1 is removed from the tissue. Under the pressure of the pressure spring 23 installed, the needle covering device 22 can be advanced relative to the casing 20 and the injection needle 1, back into its foremost position in which it protrudes beyond the injection needle 1 and covers it. The user can deliver the injection device to a collection point.

Figure 5:
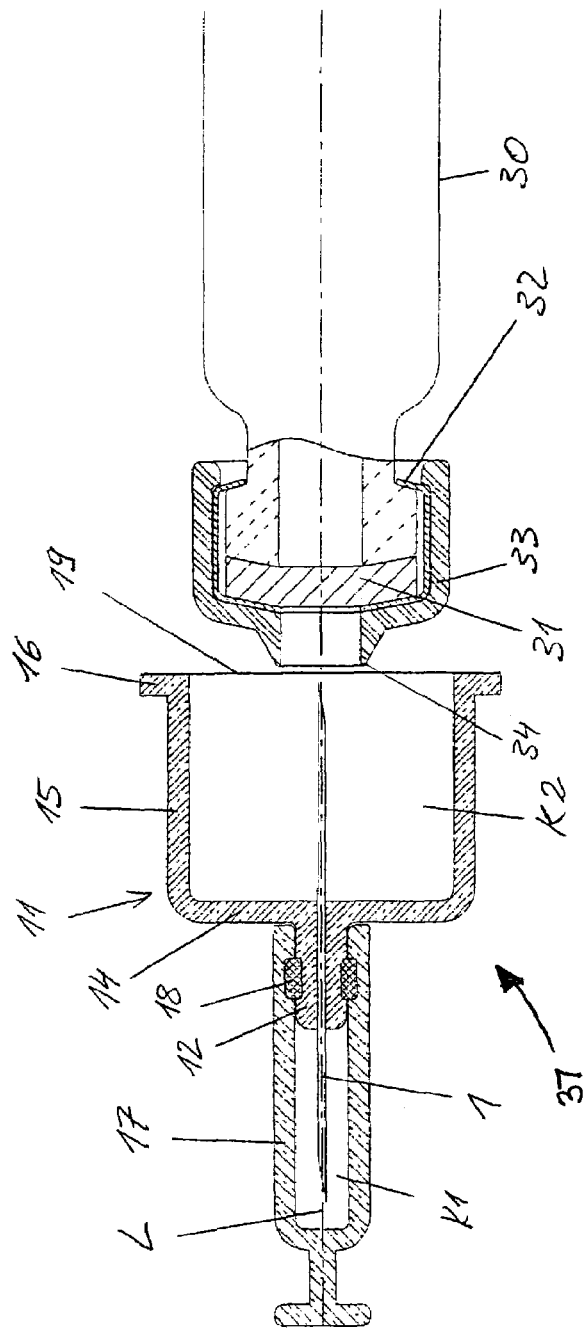
FIG. 5 depicts a needle support in a second examplary embodiment, and the ampoule of FIG. 1 in a position orientated for establishing a connection.
Figure 6:
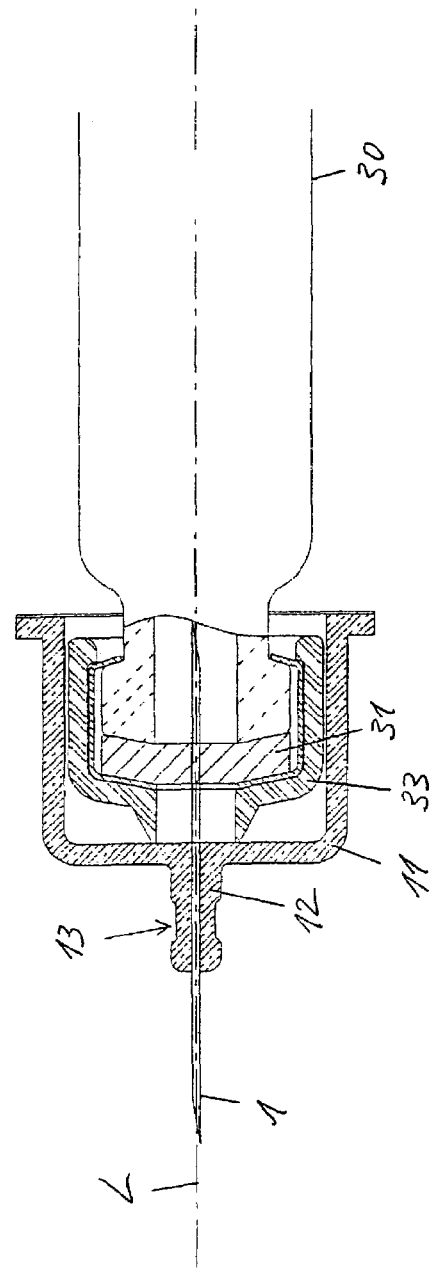
FIG. 6 depicts the needle support and the ampoule of FIG. 5, once the connection has been established.

FIGS. 5 and 6 show a needle support 37 according to a second exemplary embodiment. The needle support 37 of the second exemplary embodiment is attached into the injection device in FIGS. 3 and 4 in the same way as the needle support 39 of the first embodiment. The needle support 37 of the second embodiment co-operates with an ampoule 30 which completely corresponds to the ampoule 30 of the first embodiment. The two needle supports 39 and 37 are mutually exchangeable.

The needle support 37 of the second exemplary embodiment is also in two parts and comprises a holding body 11 and a protective cap 17.

The holding body 11 substantially exhibits the shape of a pot, comprising a circular-cylindrical surface area 15, a base 14 and a continuation 12 projecting forwards from the base 14 in the longitudinal direction of the injection needle 1. The needle 1 centrally protrudes through the base 14 and is held by the base 14 and in particular the continuation 12, such that it cannot move along the longitudinal axis L relative to the holding body 11. In some embodiments, including, the first and second embodiments, it cannot be moved at all relative to the holding body 11.

The continuation 12 serves not only to fix the injection needle 1, but also to connect the holding body 11 and the protective cap 17 in a seal. The protective cap 17 is formed by a thin hollow cylinder which is closed at its front end and is placed over the continuation 12 in a rear portion. In the overlapping region, a groove is circumferentially relieved on the inner surface area of the protective cap 17 and a sealing element 18 is inserted into said groove. Opposite the groove in the protective cap 17, a circumferential groove is also relieved on the outer surface area of the continuation 12, said groove also accommodating a part of the sealing element 18. The sealing effect of the sealing element 18 is such that the protective cap 17 forms a sterile front chamber K1 for the front needle portion of the injection needle 1. A gripping part forms the foremost end of the protective cap 17.

In the second examplary embodiment, the holding body 11 itself forms a sterile rear chamber K2 for the rear needle portion of the injection needle 1. In order to seal the rear chamber K2 sufficiently tightly to preserve the sterility, a sealing element 19 is circumferentially connected in a material lock to the holding body 11 on the rear facing area of the holding body 11, preferably, in one embodiment, by means of adhesion. The sealing element 19 is formed in the same way as in the embodiment in FIGS. 1 and 2. If gaseous exchange does not take place between the two chambers K1 and K2 around the outer surface area of the injection needle 1, the needle support 37 of the second embodiment forms two separate, sterile chambers K1 and K2. A fixing element 16 of the needle support 37 is also formed by an outer flange which, however, is formed at the rear end of the holding body 11.

By forming a fixing element 8 or 16 outside the chamber K2, the needle supports 39 on the one hand and 37 on the other can be attached with an intact rear sterile chamber K2. This is preferably designed as a rear, outer flange, however other designs are equally conceivable. The collars 6 or 14 also form fixing elements. When attached in a fixed casing, i.e., when the needle covering device 22 is omitted, the flange 8 or 16 can be omitted since the needle support 39 or 37 can simply be fixed in the longitudinal direction L between mutually opposing walls of the casing. Fixing can also be realized, for example, by means of a locking connection. For fixing in this way, at least one locking element would have to be provided as a fixing element on the needle support 39 or 37 outside the chambers K1 and K2.

If the needle support 39 is replaced in FIGS. 3 and 4 by the needle support 37, then in a first step directly before injecting, as already described, the needle covering device 22 would firstly be pressed against the collar 14 of the holding body 11. With the needle covering device 22 in this position, the user can remove the protective cap 17 forwards from the holding body 11 in the longitudinal direction. From this moment, the front needle portion of the injection needle 1 would freely protrude, as can be seen for the connected ampoule 30 and needle support 37 in FIG. 6. Handling during injecting is particularly simple in the second examplary embodiment. The injection device is pressed via the needle covering device 22 against the skin at the injection point. This pushes the needle covering device 22 backwards and the injection needle 1 presses into and through the skin to a depth which is favorable for subcutaneous injection. After injecting, the drive means is triggered. Once the drive means has been triggered, the ampoule 30 and the injection needle 1 are connected and the product is delivered in the same way as has been described for the needle support 39 of the first examplary embodiment, although there is no shifting of the holding body 11.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising an injection needle, said injection device comprising:

a) a container for an injectable product, comprising an outlet for the product at a front end sealed by a membrane, said front end comprising a container circumference;

b) said injection needle, comprising a front needle portion facing away from said container for injecting into tissue and a rear needle portion which in an initial state of the injection device lies opposite and faces said membrane and which is injected through the membrane into the container for an injection;

c) a holding body which holds the injection needle in a central needle portion and from which a front needle portion and a rear needle portion project, the holding body projecting radially from the central needle portion and extending along a length that is at least a portion of the length of the rear needle portion, such that a holding body rear chamber is formed around at least a portion of the rear needle portion, the holding body rear chamber comprising a circumference that is larger than the container circumference, such that the front end of said container is insertable into said holding body rear chamber;

d) and a hollow-cylindrical outer body which accommodates at least a portion of said holding body rear chamber so as to be movable in an advancing direction in the longitudinal direction of the injection needle, said hollow-cylindrical outer body forming a sterile front chamber for the front needle portion, said front chamber sealed by a septum and pierced by the front needle portion of the injection needle by means of a movement which the holding body performs in the advancing direction, relative to the outer body;

e) wherein an outer wall of the holding body rear chamber and an inner wall of the hollow-cylindrical outer body are parallel to the rear needle portion and abut along a length that is at least a portion of the length of the holding body rear chamber, and said walls are slidably coupled along said length, and wherein at least one of the holding body rear chamber and the hollow-cylindrical outer body forms a sterile rear chamber for the rear needle portion, said sterile rear chamber being sealed by a sealing element on its rear side facing away from the front needle portion, said sealing element spanning a sterile chamber circumference that is larger than said container circumference;

f) and wherein the front end of the container for piercing the membrane penetrates through the sealing element into the sterile rear chamber.

2. The injection device as set forth in claim 1, wherein a separating means for cutting through the sealing element is at the front end of the container.

3. The injection device as set forth in claim 1, wherein the sealing element is a film.

4. A needle support for an injection needle, said needle support comprising:

a) a holding body which holds an injection needle in a central needle portion and from which a front needle portion and a rear needle portion project, the holding body projecting radially from the central needle portion and extending along a length that is at least a portion of the length of the rear needle portion such that a holding body rear chamber is formed around at least a portion of the rear needle portion, the holding body comprising a circumference sized to receive a container for holding an injectable product;

b) and a hollow-cylindrical outer body which accommodates said holding body so as to be movable in an advancing direction in the longitudinal direction of the front needle portion and which forms a sterile front chamber for the front needle portion, said front chamber being pierced by the injection needle by means of a movement which the holding body performs in the advancing direction, relative to the outer body;

c) wherein an outer wall of the holding body rear chamber and an inner wall of the hollow-cylindrical outer body abut along a length that is at least a portion of the length of the holding body rear chamber, and said walls are slidably coupled along said length, and wherein at least one of the holding body rear chamber and the hollow-cylindrical outer body forms a sterile rear chamber for the rear needle portion said rear sterile chamber being sealed by a sealing element materially coupled along a circumference of the wall of at least one of the holding body rear chamber and the hollow-cylindrical outer body, and wherein the container for holding an injectable product penetrates through the sealing element into the sterile rear chamber.

5. The needle support as set forth in claim 4, wherein the hollow-cylindrical outer body comprises at least one fixing element arranged outside the front chamber and outside the rear chamber for operably coupling the needle support to an injection device.

6. The needle support as set forth in claim 5, wherein the hollow-cylindrical outer body is provided with a flange pointing outwardly to form the at least one fixing element.

7. The needle support as set forth in claim 4, wherein the holding body and the hollow-cylindrical outer body are detachably connected when the holding body assumes a rear position with respect to the advancing direction relative to the outer body.

8. The needle support as set forth in claim 7, wherein said detachable connection is a positive connection.

9. The needle support as set forth in claim 5, wherein the holding body is provided with a flange pointing outwardly to form the at least one fixing element.

10. The injection device as set forth in claim 1, wherein the sealing element is integrally shaped together with said holding body to form the sterile chamber for the rear needle portion.

\* \* \* \* \*

UNITED STATES PATENT AND TRADEMARK OFFICE
CERTIFICATE OF CORRECTION

PATENT NO. : 7,374,558 B2
APPLICATION NO. : 10/354882
DATED : May 20, 2008
INVENTOR(S) : Fritz Kirchhofer Page 1 of 1

It is certified that error appears in the above-identified patent and that said Letters Patent is hereby corrected as shown below:

On the title page:
In the Assignee, item (73)
　　　Name of Assignee reads: "TechPharma Licensing, AG"
　　　Should read: -- TecPharma Licensing, AG --

Signed and Sealed this

Twenty-third Day of September, 2008

JON W. DUDAS
*Director of the United States Patent and Trademark Office*